US006535288B1

(12) United States Patent
Rangarajan et al.

(10) Patent No.: US 6,535,288 B1
(45) Date of Patent: Mar. 18, 2003

(54) MACHINE READABLE CODE TO TRIGGER DATA COLLECTION

(75) Inventors: Bharath Rangarajan, Santa Clara, CA (US); Michael K. Templeton, Atherton, CA (US); Bhanwar Singh, Morgan Hill, CA (US); Khoi A. Phan, San Jose, CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 0 days.

(21) Appl. No.: 09/902,351

(22) Filed: Jul. 10, 2001

(51) Int. Cl.$^7$ ............................................... G01N 21/89
(52) U.S. Cl. ..................................................... 356/446
(58) Field of Search .................................. 356/446, 630

(56) References Cited

U.S. PATENT DOCUMENTS

| | | | |
|---|---|---|---|
| 4,794,264 A | * | 12/1988 | Quackenbos et al. .. 250/559.16 |
| 5,181,080 A | * | 1/1993 | Fanton et al. ................ 356/128 |
| 5,343,293 A | | 8/1994 | Berger et al. |
| 5,880,838 A | | 3/1999 | Marx et al. |
| 6,052,188 A | | 4/2000 | Fluckiger et al. |
| 6,104,486 A | | 8/2000 | Arimoto |

OTHER PUBLICATIONS

"Scatterometry for the Measurement of Metal Features", In Metrology, Inspection, and Process Control for Microlithography XIV, Christopher J. Raymond, Steve W. Farrer and Scott Sucher Proceedings of SPIE, vol. 3998, Feb. (2000), pp. 135–145.

"Manufacturing Considerations for Implementation of Scatterometry for Process Monitoring", In Metrology, Inspection, and Process Control for Microlighography XIV, John Allgair, Dave Benoit, Rob Hershey and Lloyd C. Litt (Motorola); Ibrahim Abdulhalim, Bill Braymer, Michael Faeyrman, John C Robinson, Umar Whitney, Yiping Xu, Piotr Zalicki and Joel Seligson (KLA–Tencor Corp.). Preecings of SPIE. vol. 3998, Feb. (2000), p. 134.

"Phase Profilometry for the 193 nm Lithography Gate Stack", In Metrology, Inspection, and Process Control for Microlighography XIV, Nickhil Jakatdar, Xinhui Niu, Junwei Bao, Costas Spanos, Sanjay Yedur and Alain Deleporte, Proceedings of SPIE, vol. 3998, Feb. (2000), pp. 116–124.

"Lithographic Process Monitoring using Diffraction Measurements", Metrology, Inspection, and Process Control for Microlithography XIV, Emmanuel M. Drege and Dale M. Byrne, Proceedings of SPIE, vol. 3998, Feb. (2000), 12 pp.

"An Integrated System of Optical Metrology for Deep Sub–Micron Lithography", Xinhui Niu, A dissertation submitted in partial satisfaction of the requirements for the degree of Doctor of Philosphy in Engineering–Electrical Engineering and Computer Sciences in the Graduate Division of the University of California, Berkeley, Spring, 1999, 153 pp., Call #308t, 1999, 324.

* cited by examiner

Primary Examiner—Constantine Hannaher
(74) Attorney, Agent, or Firm—Eschweiler & Associates, LLC (57) ABSTRACT

The present invention is directed to a system and a method for controlling a thin film formation on a moving substrate as part of a process for manufacturing an integrated circuit. The invention involves the use of scatterometry to control the thin film formation process by analyzing the thin film on the moving substrate comprising an optical indicia and a periodic analysis structure in a periodic manner. The optical indicia is spatially associated with the periodic analysis structure and is utilized in conjunction with a signaling system to determine a position of the moving substrate, whereby a repeatable analysis of a corresponding location on the moving substrate can be performed. Scatterometry permits in-situ measurements of thin film formation progress, whereby thin film formation process conditions can be controlled in a feedback loop to obtain a targeted result. Scatterometry can also be facilitated by providing a grating pattern on a non-production portion of the substrate.

31 Claims, 5 Drawing Sheets

MACHINE READABLE CODE TO TRIGGER DATA COLLECTION

TECHNICAL FIELD OF INVENTION

The present invention relates generally to the fabrication of a semiconductor device and more particularly to a system and a method for controlling processing of a moving substrate using scatterometry.

BACKGROUND OF THE INVENTION

In the semiconductor industry, performance of components, such as, for example, transistors that are fabricated in an integrated circuit, strongly depend on the precision of manufacturing small features which form the transistor and also the application of various physical parameters during processing. For example, a variability in thickness of a thin film such as a gate dielectric can lead to variations in drive current of a transistor. Drive current, the current from source to drain of a transistor, is indicative of the speed performance of the transistor. A uniform drive current in transistors across a semiconductor wafer results in a uniform speed of transistors across the wafer and a low leakage current even in conditions when the drive current is high. On the other hand, a drive current that is non-uniform across a wafer may result in a high standby current, a high leakage current and high power consumption by the integrated circuit. Drive current uniformity is sought by reducing the variability in parameters, such as gate dielectric thin film thickness, which give rise to drive current variations.

Conditions affecting the thin film thickness on a substrate being processed in a process chamber can vary in an uncontrolled manner from batch to batch, thereby causing inconsistent results. Variations in temperature, pressure, gas flow rate, and gas composition, for example, utilized in the thin film formation process can lead to significant variations in thin film thickness. A non-uniform thin film thickness resulting in a non-uniform drive current for a transistor can have a significant impact upon the quality of a resulting integrated circuit formed on the substrate.

Obtaining precision control of the thin film formation process is one challenging aspect of forming a thin film on a substrate. Prior art techniques for measuring thin film thickness on a substrate can be employed to obtain a higher degree of precision in controlling the formation of the thin film. For example, optical scattering techniques can be utilized to measure the thin film. U.S. Pat. No. 5,343,293 discloses an optical ellipsometer measurement device for measuring the thickness of oxide films on silicon wafers based upon a discernable change in polarized light passing through the film. Data obtained from the ellipsometer measurement can further be utilized to characterize the thin film formed on the substrate, and to further control the formation of the oxide film.

Some processes, however, employ a procedure wherein the substrate moves, typically in a rotational manner, within the process chamber. Rotating the substrate within the process chamber provides even exposure of the substrate to varying conditions within different regions of the process chamber, thereby increasing the thin film uniformity across the substrate. Prior art methods of utilizing optical scattering techniques are difficult to utilize on a moving substrate, however, due to the nature of measuring scattered light from a moving target.

Therefore, there remains an unsatisfied need for a system and a method that provides precise control of a formation of a thin film on a moving substrate using an optical scattering measurement technique.

SUMMARY OF THE INVENTION

The following presents a simplified summary of the invention in order to provide a basic understanding of some aspects of the invention. This summary is not an extensive overview of the invention. It is intended to neither identify key or critical elements of the invention nor delineate the scope of the invention. Its primary purpose is to present some concepts of the invention in a simplified form as a prelude to the more detailed description that is presented later.

The present invention generally relates to the fabrication of a semiconductor device and more particularly to a system and a method for controlling a thin film formation process. According to one exemplary aspect of the present invention, scatterometry is used as a tool to measure a thin film thickness on a moving substrate. Scatterometry permits in-situ measurements of thin film formation, whereby thin film formation process conditions are controlled in a feedback loop to obtain a targeted result. Scatterometry is facilitated, for example, by providing a grating pattern in a non-production region of a substrate. A signaling device is utilized to strobe the scatterometry measurement at a location on the moving substrate, whereby the substantially same location on the substrate is consistently measured.

To the accomplishment of the foregoing and related ends, the invention comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

DETAILED DESCRIPTION OF THE INVENTION

The present invention will now be described with reference to the drawings wherein like reference numerals are used to refer to like elements throughout. It should be understood that the description of these aspects are merely illustrative and that they should not be taken in a limiting sense. In the following description, for purposes of explanation, numerous specific details are set forth in order to provide a thorough understanding of the present invention. It will be evident to one skilled in the art, however, that the present invention may be practiced without these specific details. In other instances, well-known structures and devices are shown in block diagram form in order to facilitate description of the present invention. It is also to be understood that like reference numerals throughout the description imply similar functionality, however the use of like reference numerals does not necessarily imply the same device.

Figure 1:
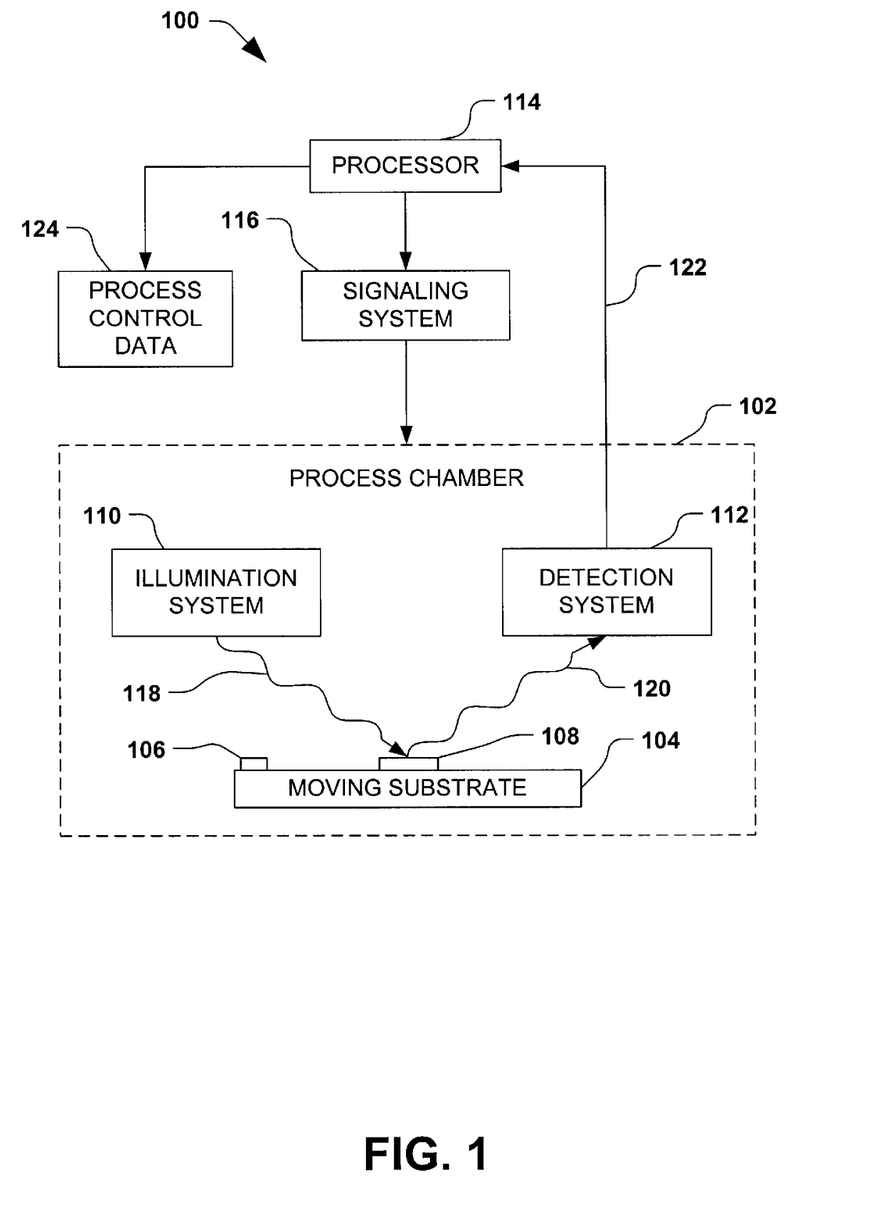
FIG. 1 is a schematic block diagram illustrating an exemplary thin film formation system with scatterometry process control according to one aspect of the present invention.

The present invention is directed to a system and a method for controlling a thin film formation process. FIG. 1 is a high level schematic of a thin film formation system 100 according to one aspect of the present invention. The thin film formation system 100 comprises a process chamber 102, and a substrate 104 (e.g., a silicon wafer), which moves with respect to the process chamber 102. Moving the substrate 104 with respect to the process chamber 102 permits a substantially even or spatially uniform thin film to be formed on the substrate 104. The substrate 104 further comprises an optical indicia 106 and a periodic analysis structure 108, wherein the optical indicia 106 and the periodic analysis structure 108 have a predetermined spatial relationship with respect to the substrate 104.

The system 100 further comprises an illumination system 110, a detection system 112, a processor 114, and a signaling system 116. The illumination system 110 is operable to direct incident radiation 118 (e.g., monochromatic light) at the substrate 104, whereby the incident radiation 118 scatters to produce scattered radiation 120. The detection system 112 is operable to detect the scattered radiation 120, and to transmit data 122 relating to the scattered radiation 120 to the processor 114. The signaling system 116 is operable to detect the optical indicia 106 on the moving substrate 104 and to provide an indication thereof to the processor 114. The processor 114 is operable to utilize the indication provided by the signaling system 116 to determine a position of the spatially-related periodic analysis structure 108. Based on the indication from the signaling system 116, the processor 114 is further operable to process the data 122 corresponding to the scattered radiation 120 from the periodic analysis structure 108, thereby generating one or more process control signals 124 to control one or more process conditions that affect a thin film formation process in the process chamber 102.

Figure 2:
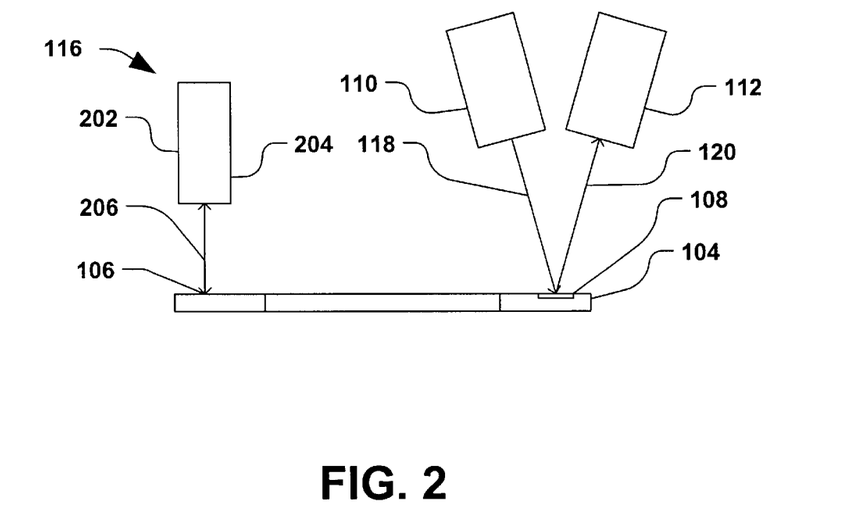
FIG. 2 is a profile-view schematic of and exemplary rotation platform retaining a substrate with a signaling device and scatterometer according to one aspect of the present invention.

According to one exemplary aspect of the present invention, the signaling system 116 determines the position of the periodic analysis structure 108 based on the optical indicia 106, wherein the optical indicia 106 comprises a distinctive artifact which is distinguishable from the remainder of the substrate 104. An exemplary substrate 104 comprising an optical indicia 106 and a periodic analysis structure 108 is illustrated in FIG. 2. The optical indicia 106 is illustrated as a series of features which can be utilized to determine, when detected, a position and spatial orientation of the substrate 104, however any feature or arrangement of features on the substrate 104 which can be utilized to determine the position and spatial orientation of the substrate 104 are contemplated and fall within the scope of the present invention.

According to one exemplary aspect of the present invention, the signaling system 116 (e.g., an optical sensor) comprises a signaling source 202 and a signaling detector 204 oriented such that an emission 206 from the signaling source 202 is substantially detected by the signaling detector 204 only when the optical indicia 106 is at a predetermined location in the movement of the substrate 104, thereby determining a position of the optical indicia 106. The determined position of the optical indicia 106 further corresponds to the spatially-related periodic analysis structure 108 on the substrate 104, whereon an analysis of a thin film is performed. Alternatively, the signaling system 116 may comprise a passive optical or radiation detector that does not employ an active signaling source.

According to another exemplary aspect of the present invention, the substrate 104 moves in a periodic or cyclical motion. For example, the substrate 104, as illustrated in plan view in FIG. 3, rotates about an axis 302. According to another exemplary aspect of the present invention, a plurality of substrates 104 reside on the platform, such that a thin film is formed on the plurality of substrates 104 within the process chamber 102, thereby allowing a higher throughput of substrates 104 in a thin film formation process. According to one exemplary aspect of the present invention, one of the plurality of substrates 104 comprises the optical indicia 106 and periodic analysis structure 108, and the analysis of the thin film formed on the one of the plurality of substrates 104 can be utilized to represent the plurality of substrates 104. According to another aspect of the present invention, a plurality of optical indicia 106 and periodic analysis structures 108 on a corresponding plurality of substrates 104 can be utilized to analyze the thin film.

Figure 3:
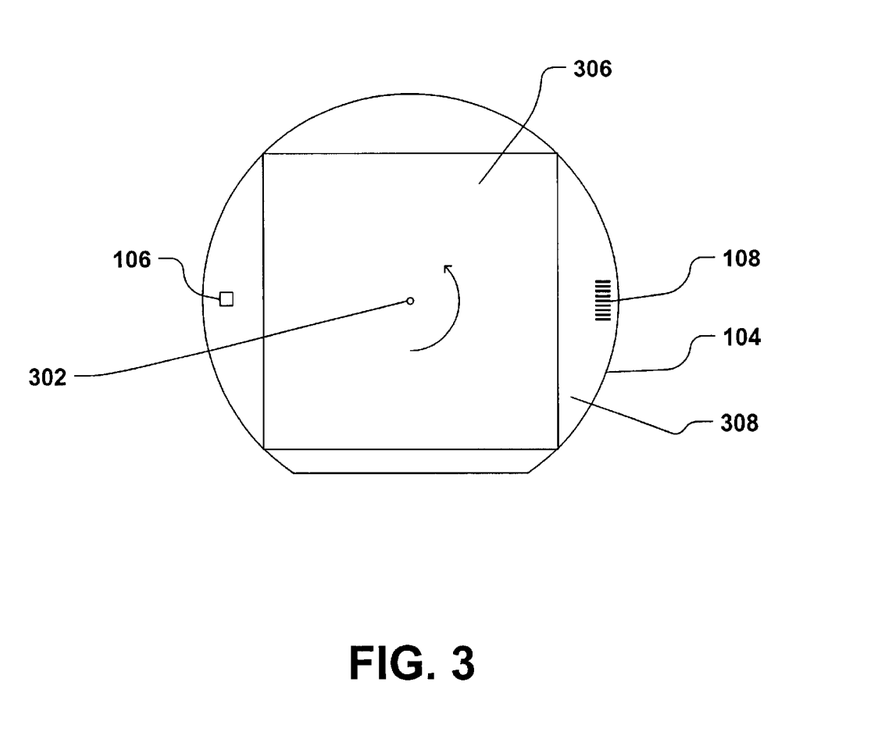
FIG. 3 is a plan-view schematic of an exemplary rotating platform retaining a substrate according to one aspect of the present invention.

According to one exemplary aspect of the present invention, an optical indicia 106 is formed in a non-production region 308 of the substrate 104. Likewise, a periodic analysis structure 108 such as, for example, a grating is formed in the non-production region 308 of the substrate 104. A non-production 308 region is herein described as a region on the substrate 104 wherein no significant components of an integrated circuit are formed. Forming the optical indicia 106 and the periodic analysis structure 108 in a non-production region 308 of the substrate 104 can be beneficial because a production region 306 is not significantly affected or reduced in area. A production region 306 is herein described as a die, or region wherein various features of an integrated circuit are formed. According to another exemplary aspect of the present invention, the optical indicia 106 is formed in a production region 306 of the substrate 104. According to another exemplary aspect, the periodic analysis structure 108 comprises features utilized in forming an integrated circuit in the production region 306. According to yet another exemplary aspect of the present invention, the optical indicia 106 and periodic analysis structure 108 are formed on a blank substrate 104 for characterization purposes. Further, a plurality of periodic analysis structures 108 comprising varying grating pitches, for example, can be formed on the substrate 104 to characterize the thin film formation process for varying thin film thicknesses.

Figure 4:
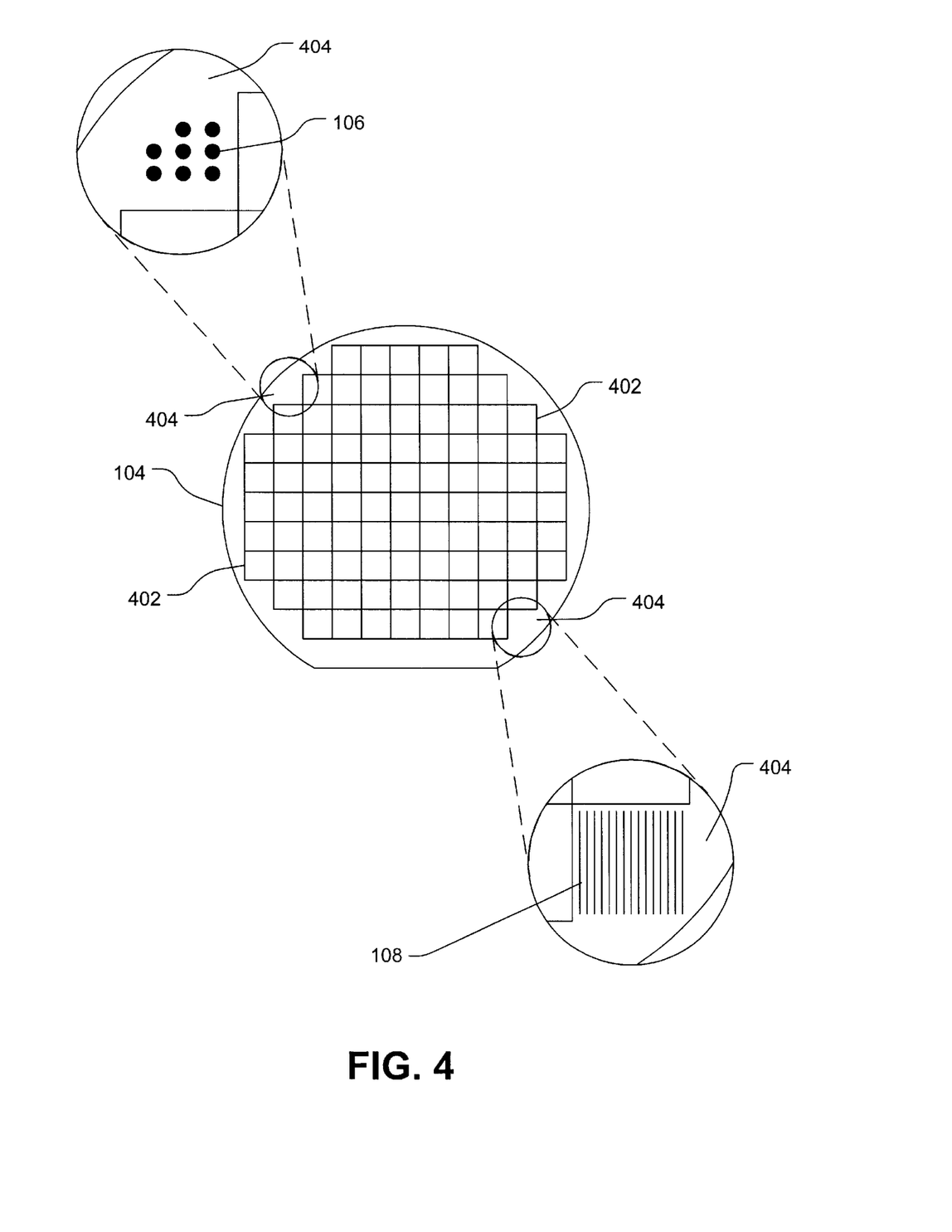
FIG. 4 is a schematic of a substrate showing production and non-production regions.
Figure 5A:
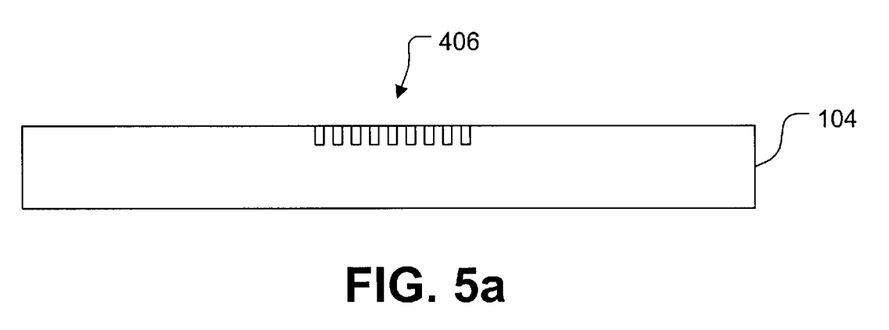
FIG. 5a is a schematic cross-section of a non-production region of a substrate having a grating associated therewith.
Figure 5B:
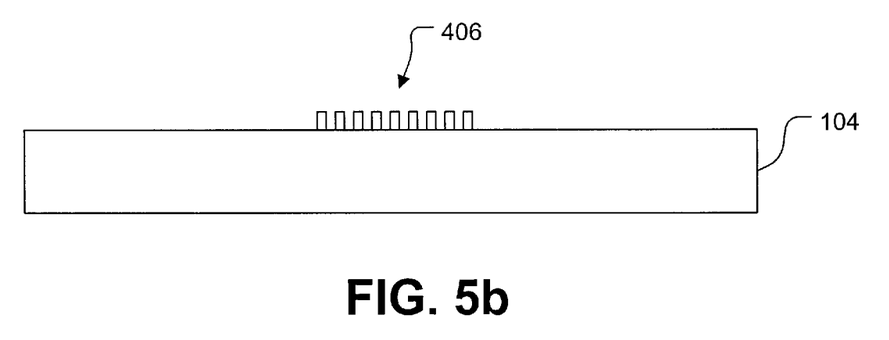
FIG. 5b is a schematic cross-section of a non-production region of a substrate having a grating associated therewith.

FIG. 4 illustrates an exemplary substrate 104 with a plurality of rectangular production regions 402 and non-production regions 404. During an exemplary integrated circuit production process, various features of an integrated circuit are formed in the production region 402, whereas a periodic analysis structure 108 such as, for example, a grating is formed in the non-production region 404 for analysis purposes. One advantage of providing a grating structure for analysis in the non-production region 404 of the substrate 104 is that the grating structure 406 can be a relatively simple structure as illustrated in FIGS. 5a and 5b in order to facilitate necessary calculations for analyzing the thin film.

According to one exemplary aspect of the present invention, the optical indicia 106 comprises a plurality of dots (e.g., recesses or mesas) arranged in a predetermined pattern as illustrated in FIG. 4. As the substrate 104 rotates, the indicia 106 will pass below a detector 116 such as an optical detector that outputs an indication signal upon detecting the pattern, thereby determining a position of the optical indicia.

Since the optical indicia 106 and the analysis structure 108 (e.g., a grating) have a predetermined spatial relationship to one another on the substrate 104, once the position of the optical indicia 106 is determined, the position of the analysis structure 108 is also known. Therefore the present invention allows for an accurate analysis of thin film formation by ascertaining an appropriate timing to collect analysis data associated with the analysis structure 108 as will be described later in greater detail.

Since the optical indicia 106 resides on the substrate 104, the thin film will also form thereon during the formation process. Therefore according to one aspect of the invention, the indicia 106 has sufficient topographical variations to provide sufficient optical contrast even after substantial film formation thereon in order to be detected.

In addition, it is appreciated that a shape of the optical indicia 106 may change during formation of the thin film. For example, for the dot pattern illustrated in FIG. 4, the diameter of the dots will grow (if the dots are raised) or shrink (if the dots comprise recessed portions) as the film forms on the substrate 104. Therefore the optical indicia detection process contemplates for such changes, for example, by detecting the center portions or centroids of each feature portion in the detection analysis. As another example, if the optical indicia 106 comprises a variable pitch grating (differing from the analysis structure 108) to resemble a bar code type indicia, since the initial pattern pitches will vary during the film formation process, a leading edge-to-leading edge type analysis, for example, may be employed in indicia detection, as may be desired.

Referring again to FIG. 3, when the substrate 104 is at the determined position as indicated by the signaling system 116, an analysis of thin film thickness at the corresponding location of the periodic analysis structure 108 is performed via the illumination system 110 and the detection system 112 of FIG. 1. FIG. 2 illustrates an exemplary orientation of an illumination system 110 and a detection system 112 with respect to the substrate 104. According to one exemplary aspect of the present invention, the illumination system 110 and the detection system 112 are components of a scatterometer. A scatterometer is a device that measures radiation such as light scattered from a surface. Scattered light includes light that is reflected and or refracted from a surface, especially light reflected or refracted from a surface with periodic features such as a grating. For a columnar light source, and where the surface is periodic, the scattered light is generally diffracted, producing inter alia a distinctive intensity distribution. The intensity may be distributed with respect to angle of incidence, angle of reflection, phase, wavelength of light, and polarity of light. The intensity distribution depends on a variety of surface characteristics, including a surface composition and geometry thereof Several types of scatterometry methodologies are available, and any such alternative scatterometry methodology is contemplated as falling within the scope of the present invention. The methodologies can be divided, for example, according to the portion of the intensity distribution analyzed to obtain information about the surface. One such exemplary methodology is 2-Θ scatterometry. Another exemplary methodology is specular spectroscopic scatterometry.

2-Θ scatterometry is based on the intensity distribution of scattered light as a function of its angle of incidence. Monochromatic radiation, such as laser light, is generally employed within an illumination system to generate an incident light 118 on the sample surface as illustrated in FIG. 1. The scattered light is distributed into diffracted orders that are located according to the formula:

$$\sin\theta_i + \sin\theta_r = \frac{m\lambda}{d}$$

where $\theta_i$ is the angle of incidence (measured relative to a vector normal to the surface), $\theta_r$ is the angle of reflection, m is the diffraction order, $\lambda$ is the wavelength of light, and d is the period of the pattern being evaluated on the surface. The $0^{th}$ diffracted order (m=0) corresponds to specular reflection, that is, scattered light that has an angle of reflection mirroring the angle of incidence. The light intensity for at least one of the diffracted orders is measured. Obtaining light intensity data from several diffracted orders provides more information, but as the grating period, d, becomes small relative to the wavelength, $\lambda$, observing diffracted orders greater than the $0^{th}$ becomes progressively more difficult. In general, observing the light intensity in just one diffracted order, the $0^{th}$ order for example, is sufficient.

Where more data is desired, the intensities of the polar components of the scattered light can be detected and examined separately. In particular, the TM component of scattered light (that with an electric field approximately parallel to the surface) exhibits one intensity distribution with respect to its angle of incidence. The TE component of scattered light (that with an electric field approximately perpendicular to the surface) exhibits another intensity distribution with respect to its angle of incidence. The TE and TM component distributions, taken together, provide more information about the surface than a single distribution that makes no distinctions based on polarity.

Specular spectroscopic scatterometry is based on the intensity distribution of the scattered light as a function of wavelength of incident light. Generally, only one angle of incidence is employed and only the $0^{th}$ diffracted order is considered, although additional data can be obtained using multiple angles of incidence and by examining diffracted orders other than the $0^{th}$. The advantage of using a single angle of incidence and examining only the $0^{th}$ diffracted order is that a single detector at a single position can be employed, thus simplifying the equipment. As with the 2-Θ technique, additional data can be obtained by separately examining the polar components of the scattered light. The light source can be monochromatic with variable wavelength. Alternatively, the light source can be polychromatic while the detection system separately detects the intensities of various wavelengths of light.

Incident light 118 is provided by the illumination system 110, which comprises, for example, one or more light sources. Depending on the scatterometry technique employed, there can be one light source at a fixed position, one light source with a variable position, or a plurality of light sources with fixed or variable positions. Generally, a single light source is sufficient. The light source can be monochromatic or polychromatic (providing white light, for example). Generally, one or more apertures are used to provide light in a columnar beam. The beam is generally broad enough to simultaneously reflect from ten or more periodic elements, or a number sufficient to produce a clear diffraction pattern.

Light intensities for scattered light 120 are measured by the detection system 112, which comprises one or more photodetectors, for example. As with the illumination system, depending on the technique involved, there can be one photodetector at a fixed position, one photodetector with a variable position, or a plurality of photodetectors with fixed or variable positions. The photodetectors can be, for example, photo-multipliers or photo-diode arrays. The detection system 112 can also include one or more polarizing filters to select TE or TM components of the scattered light 120, as may be desired.

For some configurations, the illumination system 110 and the detection system 112 may be commercially available as part of a scatterometry system. Equipment used for ellipsometry or reflectometry may also be suitable for thin film analysis.

Data 122 from the detection system 112 is provided to the processor 114, which generates one or more control signals to implement feedback control over a thin film formation process carried out in the process chamber 102. The processor 114 may include a unit manufactured specifically for use in process control. Control functions, however, may also be carried out by a general purpose computer system. Processor 114 generally includes at least a computer system, with suitable hardware and software components.

One function of the processor 114 is to relate data from the detection system 112 (light intensity data) to thin film thickness. In principle, with a few simplifying assumptions, the surface geometry of the sample being evaluated (e.g., an oxide formed on a silicon substrate) can be determined directly from the intensity data. However, the mathematics are difficult and it is generally more practical to create a database of light intensity profiles corresponding to known thin film thicknesses and search the database for a match or acceptable correlation to the light intensity measurements.

A database of light intensity profiles can be generated experimentally or a priori (by calculation). Experimentally, a plurality of thin film samples can be formed to various thicknesses. Scatterometry is performed on the samples to obtain light intensity profiles, and thin film thicknesses are determined with a technique other than scatterometry, atomic force microscopy for example. An experimentally generated database can be used with complex surface compositions and geometries, although a large number of samples may need to be generated and characterized to obtain a database large enough to support precision scatterometry measurements.

A priori approaches can be employed to generate large databases, supporting precise scatterometry measurements. Given a description of the surface geometry, the surface composition, and the properties of the component materials, light intensity profiles can be generated by any one of several techniques. In particular, Rigorous Coupled Wave Analysis (RCWA) or the Classical Model Method (CMM) can be employed in generating an a priori database.

After acquiring the light intensity data 122, the processor 114 searches the database for a match. A match is defined in a statistical sense, such as Partial Least Squares or Minimum Mean Square Error. In a large database, several profiles, corresponding to similar surface geometries, may provide a good match to the data and the closest match may be selected. With a comparatively sparse database, the measured intensity profile may fall between two database entries and an interpolation can be performed to determine the quantity of interest, which in the present context is generally the thin film thickness.

In accordance with another aspect of the present invention, the experimentally generated database may be employed to train a neural network. The processor 114 in this case is then a neural network which is trained to determine the thickness of a thin film based on the input data 122.

According to another aspect of the present invention, a spatial orientation of the substrate 104 is determined by the signaling system 116. For example, one or more sets of signaling sources 202 and/or signaling detectors 204 can be arranged such that a three-dimensional mapping of the moving substrate 104 is determined. The illumination system 110 and the detection system 112, for example, can be mounted such that a position of the illumination system 110 and detection system 112 can be controlled. Further, feedback of the spatial orientation of the moving substrate 104 is transmitted to the processor 114, wherein feedback control over the position of the illumination system 110 and the detection system 112 is carried out, such that the incident light 118 and scattered light 120 are appropriately aligned with the spatial orientation of the substrate 104.

The processor 114 or another system controller exercises control over one or more process conditions affecting a thin film formation process in the chamber 102. Any suitable thin film formation process that does not unduly interfere with scatterometry measurements can be employed. Generally, the thin film formation process is a deposition process, for example, chemical vapor deposition (CVD), or physical vapor deposition (PVD). Controllable process conditions that affect the thin film formation process can comprise, for example, flow rates of gases, pressure in the chamber, temperature, and an amount of power supplied to produce reactive ions or radicals.

According to one exemplary aspect of the present invention, the processor 114 can target the thin film formation process endpoint, terminating the thin film formation process when a desired thin film thickness is reached. In another aspect of the invention, the processor 114 provides feedback control over one or more process conditions affecting thin film formation within the process chamber, whereby a rate of thin film formation can be controlled. For example, the processor 114 can vary the kinetics of the thin film formation process by altering the relative proportions of gases and/or the temperature or pressure in the chamber in order to compensate for differences in the observed rate of thin film formation versus an expected rate of thin film formation.

The processor 114 can implement any suitable control strategy, including one of the many conventional control strategies. Conventional control strategies include, for example, proportional control, proportional-integral control, proportional-derivative control, proportional-integral-derivative control, cascade control, ratio control, override control, split-range control, time-cycle control, and program control. Optionally, the control parameters can be tuned based on a model of the thin film formation process, for example, a model that captures the dependency of thin film thickness on gas flow rate or temperature.

Figure 6:
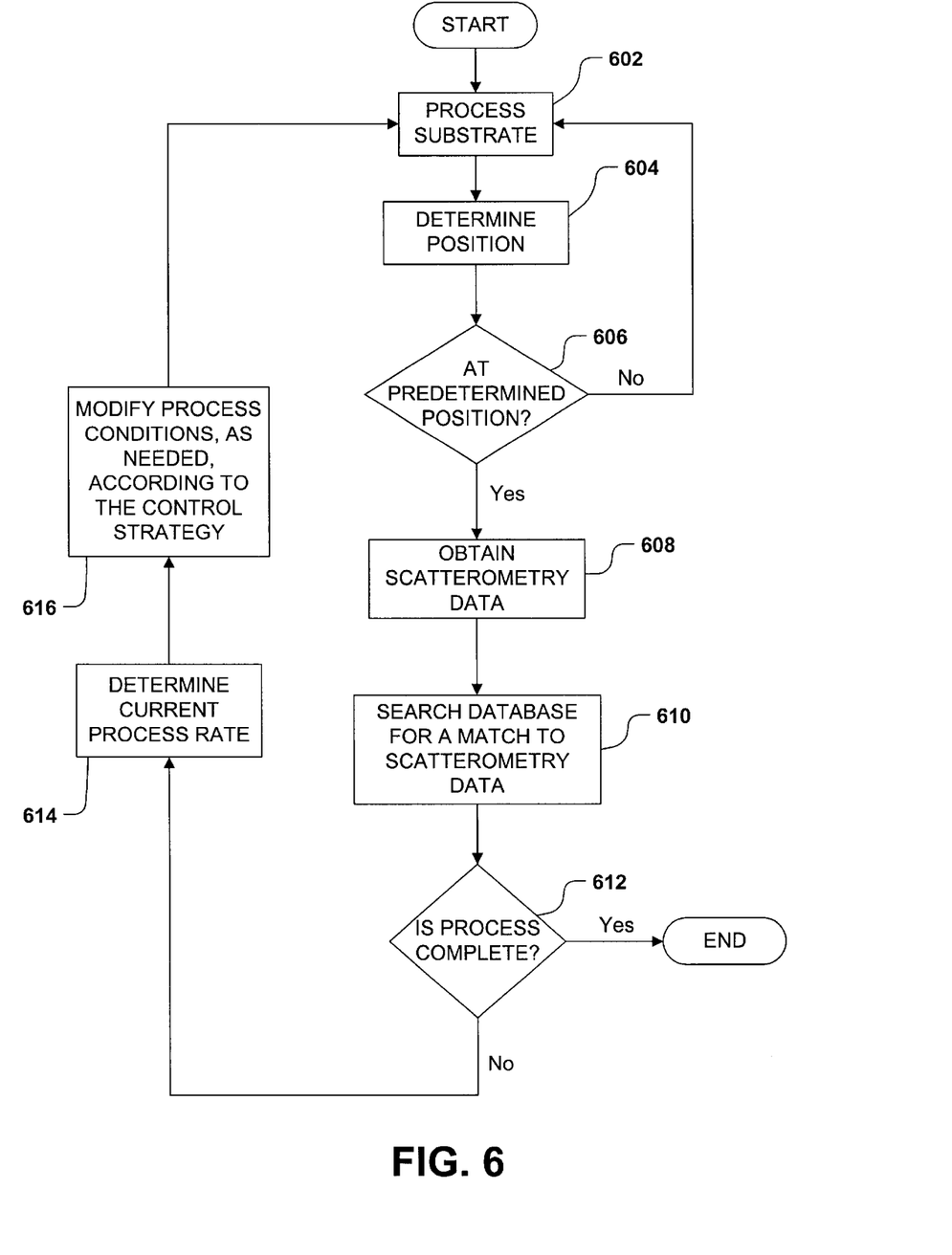
FIG. 6 is a flow chart of a method for controlling a thin film formation process on a rotating platform according to another aspect of the present invention.

FIG. 6 is a flow chart of a method 600 of forming a thin film according to a further aspect of the present invention. While exemplary methods are illustrated and described herein as a series of acts or events, it will be appreciated that the present invention is not limited by the illustrated ordering of such acts or events, as some steps may occur in different orders and/or concurrently with other steps apart from that shown and described herein, in accordance with the invention. In addition, not all illustrated steps may be required to implement a methodology in accordance with the present invention. Moreover, it will be appreciated that the methods may be implemented in association with the apparatus and systems illustrated and described herein as well as in association with other systems not illustrated.

The process begins with step 602, wherein a thin film is formed on a substrate (e.g., silicon) which comprises an optical indicia in a process chamber based on one or more process parameters. The process of forming the thin film on the substrate comprises, for example, rapid thermal processing (RTP) or a chemical vapor deposition (CVD) process whereby a thin film such as, for example, an oxide or nitride is formed on the substrate. The one or more process parameters which control at least partially the thin film formation process may comprise, for example, gas composition, gas flow rate, temperature, pressure, or amount of power employed to form the thin film on the substrate.

The substrate is moved within the process chamber (e.g., rotated therein) during the thin film formation at step 602. Moving the substrate permits a substantially even or spatially uniform thin film to be formed over the substrate. As the substrate is moved within the process chamber during processing at step 602, a signaling system is utilized to determine a position of the optical indicia at step 604.

A decision is made at step 606 to determine whether the substrate is at a predetermined position. The predetermined position corresponds to an orientation of the substrate in which the optical indicia and an associated periodic analysis structure (e.g. a grating) are at a particular location in which an analysis tool evaluates the periodic analysis structure effectively. If the signaling system indicates that the substrate is not at the predetermined position, the substrate continues to be processed at step 602. If the signaling system indicates that the substrate is at the predetermined position, the process continues to step 608, wherein the thin film formed on the substrate is analyzed at step 608.

As the thin film is formed on the substrate and the optical indicia is identified, in-situ scatterometry measurements are taken at the periodic analysis structure at step 608. These measurements are characteristic of the thickness of the thin film formed on the substrate. The measurements may be taken from one or more locations which can include production and/or non-production regions of the substrate. Scatterometry measurements can be taken either continuously, or strobed in an intermittent or periodic manner, whereby only scatterometry measurements which correspond to the predetermined position of the substrate are analyzed.

At step 610, the obtained scatterometry data is analyzed to determine the thickness of the thin film formed on the substrate. This generally involves searching a database of intensity profiles for a match to the scatterometry data. The thin film thickness is determined, for example, based on the closest match or matches in the database to the obtained data.

At step 612, a decision is made whether to terminate the thin film formation process based on the thin film thickness determination. If the analysis of the scatterometry data indicates the desired thin film thickness has been reached, the process is terminated. Otherwise, the process continues with step 614, determining the current process rate.

At step 614, the current thin film formation rate is determined for predetermined location on the substrate. The thin film formation rate can be determined by comparing a current thin film thickness to previous data regarding thin film thicknesses. For example, a thin film formation rate can be determined by subtracting a previously measured thin film thickness from the current measurement of thin film thickness and dividing by the time that elapsed between the two measurements. If control is based entirely on a thin film thickness, without reference to rate, step 614 can be omitted.

At step 616, one or more thin film formation process conditions are controlled, as needed, to implement a control strategy based on the thickness determination from the scatterometry data. A control strategy can also be based on measurements at a plurality of locations. It can also be effective, for example, to control the process with the objective of keeping the thin film formation rate at a predetermined value.

Although the invention has been shown and described with respect to certain aspects, equivalent alterations and modifications will occur to others skilled in the art upon the reading and understanding of this specification and the annexed drawings. In particular regard to the various functions performed by the above described components (systems, devices, assemblies, etc.), the terms used to describe such components are intended to correspond, unless otherwise indicated, to any component which performs the specified function of the described component (i.e., that is functionally equivalent), even though not structurally equivalent to the disclosed structure that performs the function in the herein illustrated exemplary aspects of the invention. In addition, while a particular feature of the invention may have been disclosed with respect to only one of several aspects, such feature may be combined with one or more other features of the other aspects as may be desired and advantageous for any given or particular application. Furthermore, to the extent that the term "includes" is used in either the detailed description and the claims, such term is intended to be inclusive in a manner similar to the term "comprising."

What is claimed is:

1. A system operable to form a thin film on a substrate, comprising:

a thin film formation process chamber;

a moving substrate further comprising an optical indicia and a periodic analysis structure, wherein the optical indicia and the periodic analysis structure have a predetermined spatial relationship;

a signaling system configured to determine a position of the optical indicia and provide an indication thereof;

one or more radiation sources configured to provide radiation that is directed at a surface of the moving substrate;

one or more radiation detectors configured to measure one or more properties of radiation scattered from the substrate and generate data relating to the one or more measured radiation properties; and a processor configured to receive the data relating to the one or more measured radiation properties at a timing which is a function of the indication provided by the signaling system, and to provide feedback control, based on the data, over one or more process conditions affecting a formation of the thin film within the process chamber.

2. The system of claim 1, wherein the signaling system further comprises a signaling source and a signaling detector oriented such that an emission from the signaling source is significantly detected by the signaling detector when the optical indicia is at a predetermined location, thereby determining the position of the moving substrate.

3. The system of claim 2, wherein the signaling source is a light source, and the signaling detector is a photodetector.

4. The system of claim 1, wherein the optical indicia comprises a distinctive artifact which is distinguishable from the remainder of the substrate.

5. The system of claim 1, wherein the moving substrate further rotates.

6. The system of claim 1, wherein the substrate is retained on a moving platform.

7. The system of claim 1, wherein a thin film is formed on a plurality of substrates, wherein one of the plurality of substrates comprises an optical indicia and a periodic analysis structure.

8. The system of claim 1, wherein a scatterometry system comprises the one or more radiation sources and the one or more radiation detectors.

9. The system of claim 1, wherein the processor provides one or more of proportional control, proportional-integral control, proportional-derivative control, proportional-integral-derivative control, cascade control, ratio control, override control, split-range control, time-cycle control, and program control.

10. The system of claim 1, wherein the one or more radiation sources comprise a monochromatic light source.

11. The system of claim 1, wherein the one or more radiation detectors are configured to separately measure intensities of two polar components of radiation scattered from the substrate.

12. The system of claim 1, wherein the processor comprises a component that provides a priori relationships between radiation intensity measurements and thin film thicknesses.

13. The system of claim 1, wherein the processor comprises a component that provides historical data relating radiation intensity measurements to thin film thickness.

14. The system of claim 1, wherein the substrate is silicon.

15. The system of claim 1, wherein the processor further is operable to adjust the orientation of the one or more radiation sources and the one or more radiation detectors based on a spatial orientation of the moving substrate.

16. A method of controlling a thin film formation on a moving substrate which comprises an optical indicia and a periodic analysis structure, further comprising:

employing a thin film formation process to form a thin film on the moving substrate based on one or more thin film formation process parameters;

determining a position of the optical indicia;

obtaining scatterometry data from the periodic analysis structure having a predetermined spatial relationship to the optical indicia based on the determined position of the optical indicia; and providing feedback control over the thin film formation process based on the scatterometry data, wherein the feedback control controls at least one of the one or more thin film formation process parameters.

17. The method of claim 16, wherein the moving substrate rotates.

18. The method of claim 16, further comprising forming a thin film on a plurality of substrates.

19. The method of claim 16, wherein the substrate further comprises production and non-production regions, wherein the periodic analysis structure defines one or more grating patterns over a non-production region of the substrate, and the scatterometry data is obtained by a scatterometry method that involves detecting radiation scattered from the grating pattern.

20. The method of claim 16, wherein the one or more thin film formation process parameters comprises gas composition, gas flow rate, temperature, pressure, or amount of power employed to form the thin film on the substrate.

21. The method of claim 16, wherein the feedback control comprises one or more of proportional control, proportional-integral control, proportional-derivative control, proportional-integral-derivative control, cascade control, ratio control, override control, split-range control, time-cycle control, and program control.

22. The method of claim 16, wherein the feedback control comprises analyzing the scatterometry data using a priori relationships between light intensities and thin film thicknesses.

23. The method of claim 16, wherein the feedback control comprises comparing the scatterometry data to historical data relating scatterometry measurements to thin film thickness.

24. The method of claim 16, wherein the scatterometry data is obtained by a method involving one or more monochromatic light sources and one or more photodetectors configured to separately measure the intensities of two polar components of light scattered from the substrate.

25. The method of claim 24, wherein the one or more monochromatic light sources remain on throughout the movement of the substrate while the one or more photodetectors are strobed on when the substrate is at a predetermined position, whereby scatterometry data is collected only at the predetermined position.

26. The method of claim 24, wherein the one or more monochromatic light sources and the one or more photodetectors are strobed on when the substrate is at a predetermined position, whereby scatterometry data is collected only at the predetermined position.

27. The method of claim 24, wherein the one or more monochromatic light sources and the one or more photodetectors remain on throughout the formation of the thin film on the substrate, wherein scatterometry data is collected throughout the thin film formation and evaluated at a time interval associated with the predetermined position of the substrate.

28. The method of claim 24, wherein the feedback control over the thin film formation process is based on the scatterometry data at a predetermined position of the substrate.

29. The method of claim 16, wherein the substrate is retained on a moving platform.

30. The method of claim 16, wherein determining the position of the optical indicia comprises emitting illumination from a signaling source onto the moving substrate and detecting the illumination by a signaling detector.

31. The method of claim 30, wherein the signaling source is a light source, and the signaling detector is a photodetector.

* * * * *